United States Patent [19]

Reid, Jr.

[11] Patent Number: 4,800,870
[45] Date of Patent: Jan. 31, 1989

[54] METHOD AND APPARATUS FOR BILE DUCT EXPLORATION

[76] Inventor: Ben A. Reid, Jr., 4001 Dutchmans La., Louisville, Ky. 40207

[21] Appl. No.: 166,923

[22] Filed: Mar. 11, 1988

[51] Int. Cl.⁴ .............................................. A61B 1/06
[52] U.S. Cl. ..................................................... 128/6
[58] Field of Search ............................ 128/3, 4, 5, 6, 7

[56] References Cited

U.S. PATENT DOCUMENTS

| | | | |
|---|---|---|---|
| 3,572,325 | 3/1971 | Bazell et al. | 128/6 |
| 3,739,770 | 6/1973 | Mori | 128/6 |
| 4,245,624 | 1/1981 | Komiya | 128/4 |
| 4,279,245 | 7/1981 | Takagi et al. | 128/4 |
| 4,351,323 | 9/1982 | Ouchi et al. | 128/4 |
| 4,601,283 | 7/1986 | Chikama | 128/4 |
| 4,607,622 | 8/1986 | Fritch et al. | 128/6 |

Primary Examiner—William H. Grieb
Attorney, Agent, or Firm—Larson & Taylor

[57] ABSTRACT

A method and apparatus for exploration of the bile duct is provided wherein an endoscope having a probe of sufficiently small diameter to be inserted into the cystic duct is utilized. The probe has channels therein including conventional illuminating, viewing and irrigation facilities. In addition, a separate passageway is provided for a malleable stylet. This malleable stylet gives the scope the necessary rigidity and shape to be introduced and controlled precisely within the bile duct while at the same time allows the scope to be individually reconfigured as needed during an operation to meet the particular anatomical needs of a patient.

4 Claims, 2 Drawing Sheets

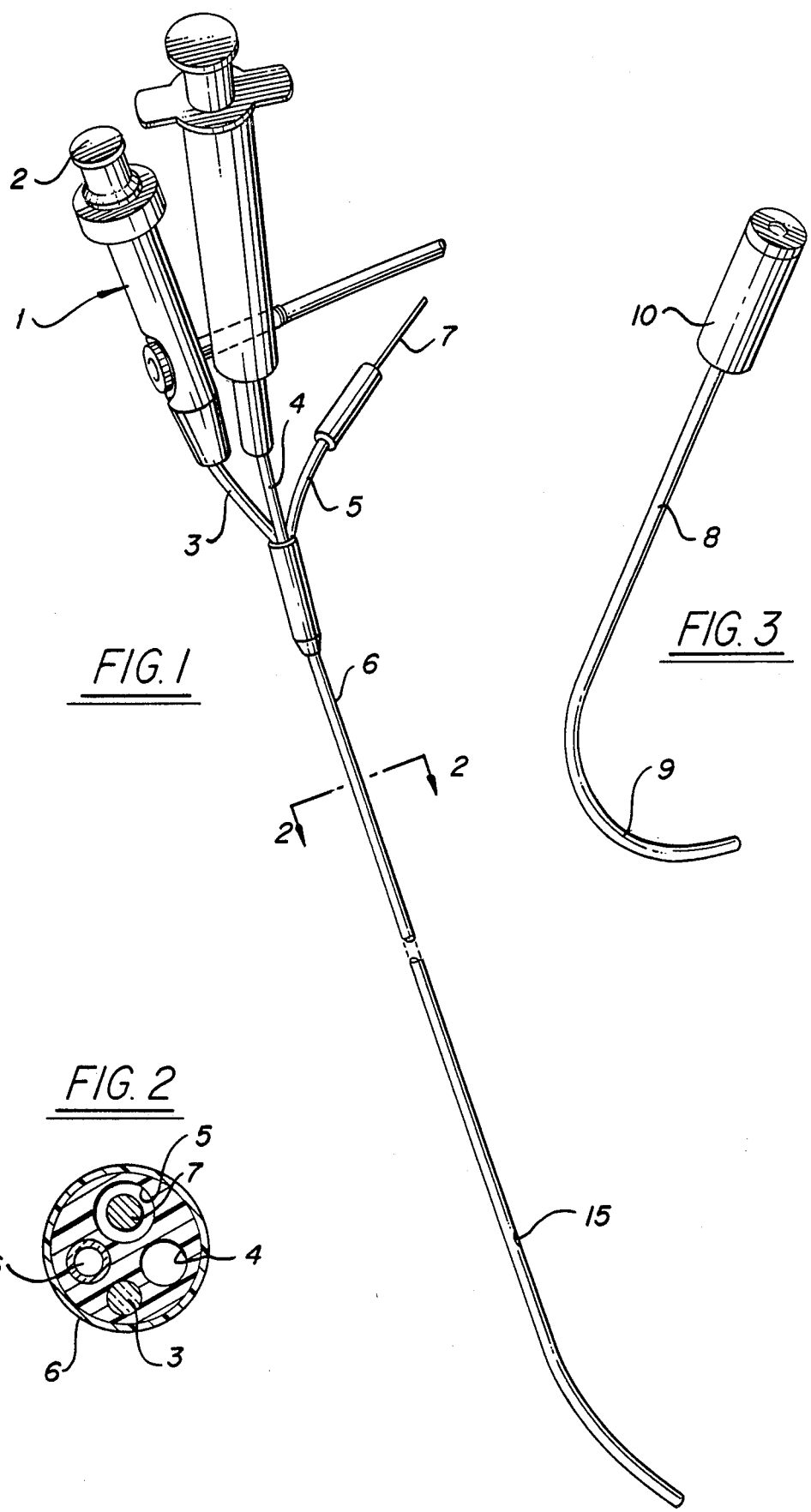

METHOD AND APPARATUS FOR BILE DUCT EXPLORATION

BACKGROUND OF THE INVENTION

The present invention relates to a method and apparatus for permitting exploration of the common bile duct through the cystic duct by use of a malleable stylet disposed in a small diameter probe of an endoscope.

Heretofore, the conventional method and apparatus for examining the common bile duct comprised opening the bile duct and inserting a Bake's dilator within the duct. The Bake's dilator generally comprises a malleable rod having a handle on one end and an enlarged distal end. The rod portion of the dilator may be bent so that the surgeon may hold the handle while the distal end is within the duct. The dilator is passed through the common bile duct, and any stone within the duct will be felt by the surgeon although he cannot see the stone within the duct. Once the stone is detected, it may be removed by either pressing against it with the dilator and moving it down the duct and through the passageway into the intestine or, alternatively, the dilator may be removed and another instrument suitable for gripping the stone may be inserted to grasp the stone and withdraw it through the opening into the bile duct.

While the above-described prior art method and apparatus for exploration of the bile duct has been successfully used, it has many limitations. In the first place, it requires opening of the bile duct itself increasing the risk and duration of the surgery rather than using the already open smaller cystic duct. In addition, the surgeon cannot readily determine whether his operation with the Bake's dilator has successfully removed all stones from the bile duct as, for example, smaller stones may pass around the distal end of the dilator as it is being moved through the bile duct. Thus, the use of the Bake's dilator for biliary tract exploration is not always entirely satisfactory.

Endoscopes have been used extensively in connection with the examination of ducts or passageways within the body. However, heretofore, it has not been possible to provide an endoscope which is entirely suitable for use in connection with determining the condition of the interior of the common bile duct. The problem has been that conventional endoscopic equipment is too large to pass through a normal diameter common bile duct. When the bile duct is abnormally large enough to accept these scopes, there are still problems. The rigid scope with its fixed dimensions can only visualize limited areas of the extremely variable bile duct, while the very flexible scopes are difficult to stabilize and therefore difficult to direct through these serpentine ducts.

In the prior art there have been provided endoscopes with steering means for directing the distal end of the probe on the endoscope. Typical of these devices are the endoscopes disclosed in U.S. Pat. Nos. 3,572,325; 3,739,770; 4,245,624 and 4,351,323. All of the foregoing patents disclosed various types of mechanical means for directing the path of the distal end of an endoscope. While these devices are useful in connection with the use of an endoscope in relatively large ducts, such as the intestine, it is impossible to incorporate such mechanism within an endoscope suitable for passage through a cystic or common bile duct of normal diameter.

U.S. Pat. No. 4,601,283 discloses a probe for an endoscope which is provided with a shape memory alloy whereby the flexible tube may be inserted through the bent portions of a passageway and, when it is desired to give the tube rigidity, a heating wire heats the memory alloy to its original shape to provide rigidity to the flexible end of the probe. This method and apparatus for inserting a probe into a passageway within the body could not be used in connection with examination of the bile duct due to the size constraints of exploratory operations within the bile duct and due to the extreme flexibility of a probe small enough to fit within the cystic duct.

SUMMARY OF THE INVENTION

The present invention provides a method and apparatus for examining the bile duct by using an endoscope having a small diameter probe with means in the probe for preshaping the distal end of the probe so that it is possible to enter an opening in the cystic duct and pass from the cystic duct into the bile duct and thus permit a complete exploration of the interior of the bile duct. According to the present invention, a malleable stylet disposed within a channel is included within the conventional elements within the probe. At present there are two versions. One in which the scope image is viewed directly through the scope optical handle. Here the malleable stylet extends the entire length of the probe and is controlled from the optical handle. A second version is viewed through a TV monitor. This allows the malleable stylet to enter the probe near its working distal end (intra ductal segment of scope) making for a much shorter and therefore more easily controlled stylet and probe. The unique structure of the endoscope probe, according to the present invention, provides for close examination of the entire bile duct to an extent not heretofore possible. Furthermore, it permits the surgeon to visually observe stones within the duct to insure that any operative procedure is effective and conclusive.

BRIEF DESCRIPTION OF THE DRAWINGS

FIG. 1 is a perspective view of an endoscope with a probe including a stylet according to the present invention, FIG. 2 is a cross sectional view of the probe along the lines 2—2 of FIG. 1, FIG. 3 is a perspective view of a modified form of stylet, FIGS. 4(a), (b) and (c) are sequential diagrammatic views demonstrating the insertion of the probe into the bile duct.

DETAILED DESCRIPTION OF THE DRAWINGS

Figure 4A:
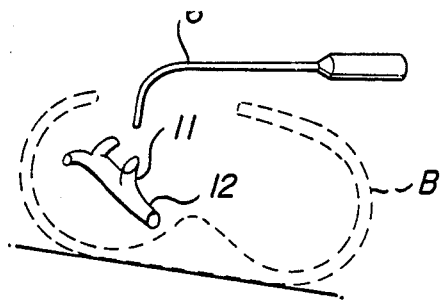

Referring now more specifically to the drawings wherein like numerals indicate like parts throughout the several views, there is shown at 1 in FIG. 1 an endoscope which includes a handle portion which is conventional and contains a focusing lens 2 at the proximal end and has a cable 3 extending from the distal end thereof which contains the light fiber bundle and the viewing fiber bundle. As shown in FIG. 1, there is further provided an irrigation and suction channel 4 and a stylet channel 5 which extends into the proximal end of the encasing flexible hollow probe 6.

In FIG. 2, there is shown a cross sectional view of the probe, and the cable containing the fiber optic bundle 16 and light bundle 3 is shown as well as the irrigation and suction channel 4 and stylet channel 5. The overall diameter of the probe is approximately 2 millimeters, and the probe itself may be of any desired length and in one embodiment is approximately 25 centimeters long with viewing through the optical handle and a second version 45 centimeters long which is viewed through a TV monitor.

The stylet channel 5 contains a stylet 7, which comprises a fine wire which is malleable and will retain any desired configuration into which the stylet is bent. The stylet is of a length greater than the length of the probe so that it extends outwardly beyond the proximal end of the stylet channel 5. This permits manipulation of the stylet 7 within the probe 6.

An alternative form of stylet is shown in FIG. 3 which is used in the 45 centimeter long scope whose image is viewed through a TV monitor. Stylet 8 is, as shown, relatively short and may be passed into an opening 15 within the probe 6 adjacent the distal end of the probe. Thus, the surgeon may grasp the handle 10 and control the distal intraductal end of the probe.

The apparatus described with the stylet channel 5 and fine malleable wire stylet 7 is used specifically in connection with biliary exploration. Without the stylet the small diameter probe 6, which is essential in order to enter the common bile duct through the cystic duct, is so flexible that it cannot be maneuvered readily through the ducts as it tends to fold or bend upon itself. The malleable stylet 7 gives the probe sufficient rigidity and shape to permit the surgeon to maneuver the probe within the ducts to perform the necessary procedures.

Figure 4B:
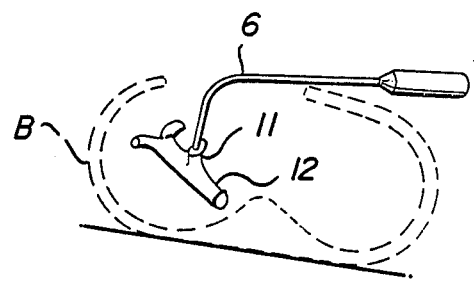
Figure 4C:
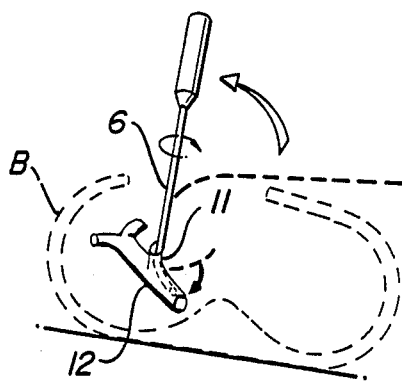

Referring now to FIGS. 4(a), (b) and (c), the method of using the presently disclosed endoscope and biliary probe is shown. The patient's body is diagramaticaaly shown as B and the cystic duct 11 and common bile duct 12 are shown in correct orientation within the body in FIG. 4(a). The cystic duct 11 is severed approximately 1 centimeter from the common bile duct 12 so that the distal end of the probe 6 can be inserted through the cystic duct into the common bile duct. As shown in FIG. 4(a), the probe 6 has a curved portion adjacent the distal end so as to permit the probe to be inserted into the cystic duct and pass around the bend in the cystic duct as it joins the common bile duct. The bend in the probe is formed by shaping the end portion of the stylet into the desired curvature. The stylet is then inserted in the stylet channel, and the stiffness of the stylet insures that the probe will follow the contour of the stylet. In the position shown in FIG. 4(b), the endoscope handle and the major portion of the length of the probe extends substantially parallel to the table surface upon which the patient is lying. As shown in FIG. 4(b), the distal end of the probe extends downwardly at substantially a right angle with respect to the remainder of the probe. As shown in FIG. 4(b), the entire scope is then moved toward the patient with the tip of the probe entering the cystic duct. As shown in FIG. 4(c), the endoscope is then swung upwardly, so as to bring the distal end of the probe into alignment with the length of the common bile duct, so that the surgeon can then view the bile duct through the endoscope lens.

By viewing through the endoscope, the surgeon can see stones, air bubbles, or any tumors which may be located within the common bile duct. At the end of the common bile duct is the ampulla of Vater, which forms the lumen between the common bile duct and the duodenum (not shown). The distal end of the scope can be moved down the common bile duct to dilate the ampulla of Vater. After dilation, small stones, biliary debris and air bubbles can usually be flushed from the duct into the duodenum. Larger stones can be manipulated through the ampulla of Vater by utilizing the tip of the scope by reason of the degree of rigidity given to the probe 6 by the stylet 7.

Figure 5:
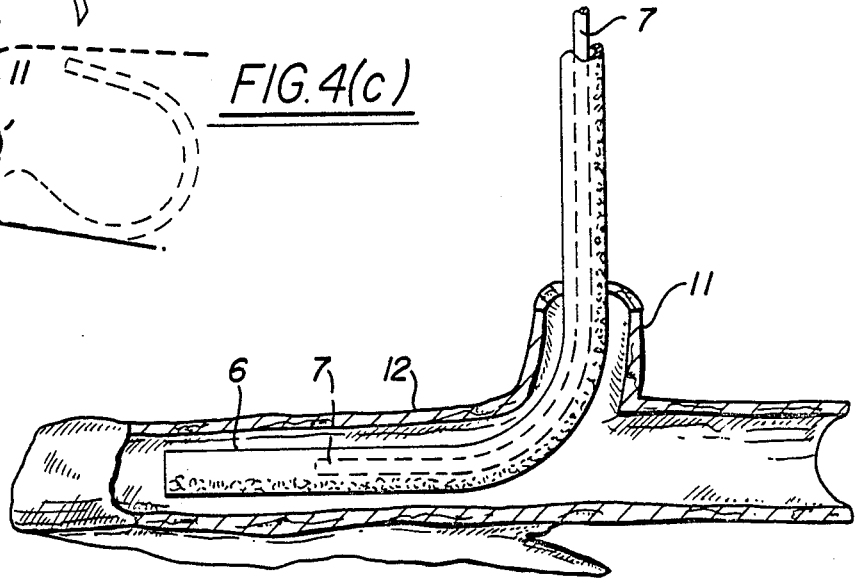
FIG. 5 is a partial cross sectional view showing a method of using the probe according to the present invention.

As seen in FIG. 5, the distal end of the probe 6 can be moved beyond the end of the stylet 7. This is achieved by grasping the proximal end of the stylet 7 and moving the instrument downwardly so that the stylet 7 is displaced inwardly from the end of the probe 6. This effectively lengthens the intraductal portion of the probe when needed to visualize a long common bile duct. If a longer, more rigid scope is necessary, the scope may be removed from the patient and the stylet removed from the scope and reshaped to the new requirements. The stylet may then be replaced into the scope, giving the surgeon a scope which is tailored to match the requirements of the particular patient being operated upon.

Figure 6:
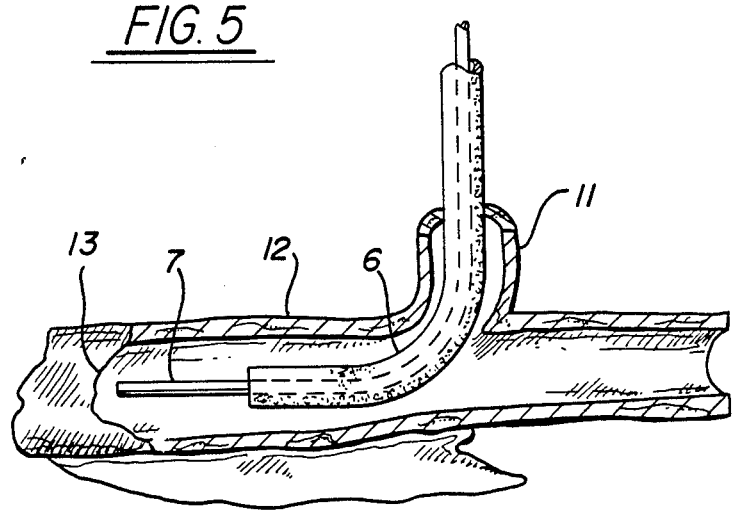
FIG. 6 is a partial cross sectional view showing an alternative use of the probe.

Referring to FIG. 6, it can be seen that the end portion of the stylet 7 extends beyond the distal end of the probe 6. This is achieved by grasping the proximal end of the stylet and holding it while moving the scope and probe away from the patient. The purpose in this procedure is to shorten the intraductal portion of the probe and is used primarily to visualize the common bile duct immediately adjacent to the cystic duct entrance.

In this configuration (stylet 7 advanced beyond the probe 6) the stylet can be used to mechanically probe intraductal stones, tumors, or ductal strictures under direct visualization as shown in FIG. 6.

It can be appreciated that the probe end can be removed from the cystic duct and inserted in the opposite direction to permit inspection of the opposite end of the bile duct shown in FIGS. 4–6.

Obviously, many modifications and variations of the present invention are possible in light of the above teachings.

What is claimed as new and as desired to be secured by Letters Patent:

1. A method of examining the bile duct of a patient utilizing an endoscope having a probe including a light fiber bundle, a viewing fiber bundle, an irrigating channel and a malleable stylet channel comprising the steps of shaping the distal end of a malleable stylet to a curved configuration so as to fit within the cystic duct of a patient, opening the cystic duct of the patient and inserting the distal end of the endoscope probe within the opened cystic duct, moving the distal end of the probe into the bile duct and examining the bile duct through the viewing fiber bundle.

2. A method, according to claim 1, and including the further step of withdrawing the probe partially from the bile duct while maintaining the stylet in the initial position thereof to shorten the intraductal portion of the scope and permit examination of areas of the bile duct immediately adjacent the cystic duct.

3. A method, according to claim 1, and including the further step of extending the distal end of the probe beyond the end of the stylet while maintaining the stylet in the initial position thereof to lengthen the intraductal portion of the scope and permit closer visualization of the ampulla of Vater and areas of the common bile duct immediately adjacent thereto.

4. A method, according to claim 1, wherein the distal end of the malleable stylet is curved so that the distal end thereof extends substantially normally with respect to the remaining portion of the stylet and the distal end of the probe is inserted in the cystic duct and the endoscope and remaining portion of the probe are pivoted to bring the distal end of the probe into the common bile duct.

* * * * *